US012630351B2

(12) United States Patent　　　(10) Patent No.:　US 12,630,351 B2
　　　Biswal et al.　　　　　　　　　(45) Date of Patent:　May 19, 2026

(54) TEMPERATURE-PROTECTIVE PACKAGE WITH SHAPE-CONFORMING PHASE CHANGE MATERIAL (PCM)

(71) Applicant: Edwards Lifesciences Corporation, Irvine, CA (US)

(72) Inventors: Amrut Nandan Biswal, Tustin, CA (US); Arti Prasad Roth, Lake Forest, CA (US); Vipul P. Rajpara, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 18 days.

(21) Appl. No.: 18/057,099

(22) Filed: Nov. 18, 2022

(65) Prior Publication Data

US 2023/0084738 A1　　　Mar. 16, 2023

Related U.S. Application Data

(63) Continuation of application No. PCT/US2021/032462, filed on May 14, 2021.

(Continued)

(51) Int. Cl.
B65D 81/32　　　　(2006.01)
A61B 50/33　　　　(2016.01)
B65D 81/38　　　　(2006.01)

(52) U.S. Cl.
CPC .......... B65D 81/3895 (2013.01); A61B 50/33 (2016.02); B65D 81/3844 (2013.01)

(58) Field of Classification Search
CPC ... A61B 50/33; A61B 50/20; A61B 2050/001; A61B 2050/0014; A61B 2050/0016;

A61B 2050/0017; A61B 2050/0018; A61B 2050/3008; A61B 2050/314; A61B 2050/316; A61B 2050/318; B65D 81/382; B65D 81/3895; B65D 81/3872;

(Continued)

(56) References Cited

U.S. PATENT DOCUMENTS 3,580,065 A　　5/1971　Strittmater et al.
3,754,700 A　　8/1973　Bonk
(Continued)

FOREIGN PATENT DOCUMENTS

CN　　102507438 A　　6/2012
CN　　107062971 A　　8/2017
(Continued)

*Primary Examiner* — Allan D Stevens
(74) *Attorney, Agent, or Firm* — Chang and Hale LLP

(57)　　　　　　ABSTRACT

A temperature-protective package includes a rigid container configured to receive a temperature-sensitive product. A flexible liner is attached to the rigid container such that a pocket is formed between the rigid container and the flexible liner. Phase change material (PCM) is situated in the pocket. The PCM conforms to a contoured surface of the rigid container. In an alternative implementation, a temperature-sensitive package includes a pocket of PCM within a flexible liner. The flexible liner defines a preferred shape of the temperature-protective package. The flexible liner also defines an opening for receiving a product. The opening corresponds to the preferred shape. In one implementation, multiple flexible liners can be utilized to define the preferred shape and the opening.

18 Claims, 7 Drawing Sheets

Related U.S. Application Data

(60) Provisional application No. 63/026,379, filed on May 18, 2020.

(58) Field of Classification Search
CPC ....... F25D 2303/0821; F25D 2303/083; F25D 2303/0831; F25D 2303/0841; F25D 2303/0845; F25D 2303/0843; F25D 2303/084; F25D 2303/0832
See application file for complete search history.

(56) References Cited

U.S. PATENT DOCUMENTS

| | | | | |
|---|---|---|---|---|
| 4,057,144 | A | 11/1977 | Schuster | |
| 5,178,267 | A | 1/1993 | Grabenkort et al. | |
| 5,335,775 | A | 8/1994 | Scanlon et al. | |
| 5,762,202 | A | 6/1998 | Atad | |
| 5,804,266 | A * | 9/1998 | Salyer | B65D 81/3453 |
| | | | | 165/53 |
| 5,881,902 | A | 3/1999 | Ackermann | |
| 5,884,006 | A | 3/1999 | Frohlich et al. | |
| 5,922,162 | A | 7/1999 | Brugger et al. | |
| 5,934,099 | A | 8/1999 | Cook et al. | |
| 6,216,885 | B1 | 4/2001 | Guillaume | |
| 6,361,746 | B1 * | 3/2002 | Wlodarski | B01L 7/00 |
| | | | | 422/561 |
| 6,644,383 | B2 | 11/2003 | Joseph et al. | |
| 6,793,078 | B2 | 9/2004 | Roshdy | |
| 7,257,963 | B2 | 8/2007 | Mayer | |
| 7,328,583 | B2 | 2/2008 | Hillman et al. | |
| 8,448,809 | B2 | 5/2013 | Kelly | |
| 8,807,373 | B1 * | 8/2014 | Russell | A47G 23/06 |
| | | | | 220/359.1 |
| 9,751,682 | B2 | 9/2017 | Mayer et al. | |
| 9,834,365 | B2 | 12/2017 | Pointer et al. | |
| 10,063,096 | B2 * | 8/2018 | Rejman | H01M 10/44 |
| 10,424,821 | B2 | 9/2019 | Iyengar et al. | |
| 10,501,254 | B2 | 12/2019 | Wood et al. | |
| 11,242,175 | B2 * | 2/2022 | Barfoot | B65D 81/3818 |
| 12,195,226 | B2 * | 1/2025 | Zou | B65D 77/0493 |

| | | | | |
|---|---|---|---|---|
| 2002/0096056 | A1 * | 7/2002 | Hopkins | B65D 81/3453 |
| | | | | 99/425 |
| 2003/0172671 | A1 * | 9/2003 | DeMars | F25D 31/006 |
| | | | | 62/457.2 |
| 2004/0079794 | A1 | 4/2004 | Mayer | |
| 2005/0000373 | A1 * | 1/2005 | Coe | F25D 3/08 |
| | | | | 99/567 |
| 2006/0156756 | A1 * | 7/2006 | Becke | A47J 41/0044 |
| | | | | 62/457.3 |
| 2006/0196497 | A1 | 9/2006 | Dean | |
| 2007/0028642 | A1 * | 2/2007 | Glade | A61B 90/98 |
| | | | | 62/457.2 |
| 2007/0186580 | A1 * | 8/2007 | Kaplan | A23L 3/36 |
| | | | | 62/530 |
| 2008/0202254 | A1 | 8/2008 | Deng et al. | |
| 2009/0152158 | A1 | 6/2009 | Kidd et al. | |
| 2010/0006578 | A1 * | 1/2010 | Roth | F25D 3/08 |
| | | | | 220/592.01 |
| 2011/0233092 | A1 * | 9/2011 | Slattery | B65D 1/36 |
| | | | | 206/427 |
| 2012/0103081 | A1 | 5/2012 | Hoshino | |
| 2015/0059488 | A1 | 3/2015 | Chang et al. | |
| 2015/0151893 | A1 | 6/2015 | Wengreen et al. | |
| 2016/0347532 | A1 | 12/2016 | McCormick | |
| 2017/0082342 | A1 * | 3/2017 | Weinberg | B65D 25/2805 |
| 2017/0333668 | A1 * | 11/2017 | Cully | A61K 39/3955 |
| 2018/0213944 | A1 * | 8/2018 | Bedel | A47C 21/044 |
| 2019/0077575 | A1 * | 3/2019 | Tilman | B65D 81/382 |
| 2019/0285326 | A1 * | 9/2019 | Berger | F25C 1/243 |
| 2019/0308788 | A1 * | 10/2019 | Matusz | B65D 85/36 |
| 2020/0329702 | A1 * | 10/2020 | Pensak | B01L 7/04 |

FOREIGN PATENT DOCUMENTS

| | | | | | |
|---|---|---|---|---|---|
| DE | 102017111702 | A1 | 11/2017 | | |
| EP | 0597769 | A1 | 5/1994 | | |
| JP | 2013174479 | A | 9/2013 | | |
| KR | 101816148 | B1 | 1/2018 | | |
| WO | WO-2010143958 | A2 * | 12/2010 | | F25D 3/08 |
| WO | WO-2014067927 | A1 * | 5/2014 | | B65D 81/382 |
| WO | WO-2023167982 | A2 | 9/2023 | | |

* cited by examiner

TEMPERATURE-PROTECTIVE PACKAGE WITH SHAPE-CONFORMING PHASE CHANGE MATERIAL (PCM)

CROSS REFERENCE

This application claims the benefit of PCT/US2021/032462, filed May 14, 2021, which claims the benefit of U.S. Patent Application No. 63/026,379, filed May 18, 2020, the entireties of which are hereby incorporated by reference.

BACKGROUND

Bioprosthetic tissue products are delicate. In particular, bioprosthetic heart valves are temperature-sensitive. For example, a bioprosthetic heart valve may be rendered unusable by exposure to temperatures below one degree Celsius (1° C.) or above forty-five degrees Celsius (45° C.). Packaging such temperature-sensitive products for storage or shipment must employ temperature protection. In a conventional approach, the temperature-sensitive product is situated in an inner container, and numerous temperature-protective packs are packed around the inner container in an outer container. In another approach, a container includes an additional compartment filled with water-based gels that act as refrigerants for the temperature-sensitive product. These packaging approaches are often bulky due to the use of additional containing volumes, and heavy due the high density of gel refrigerants, resulting in increased shipping costs. These packaging approaches are also time-consuming to assemble and disassemble, resulting in customer dissatisfaction. Complexity is further increased where the temperature-sensitive products are integrated with other products, such as delivery systems for prosthetic heart valves. Accordingly, what is needed is a temperature-protective package that minimizes volume, weight, and assembly time, while accommodating integrated products.

SUMMARY

There are provided temperature-protective packages with shape-conforming phase change material (PCM), substantially as shown in and/or described in connection with at least one of the figures, and as set forth more completely in the claims.

DETAILED DESCRIPTION

Figures 1A, 1B:
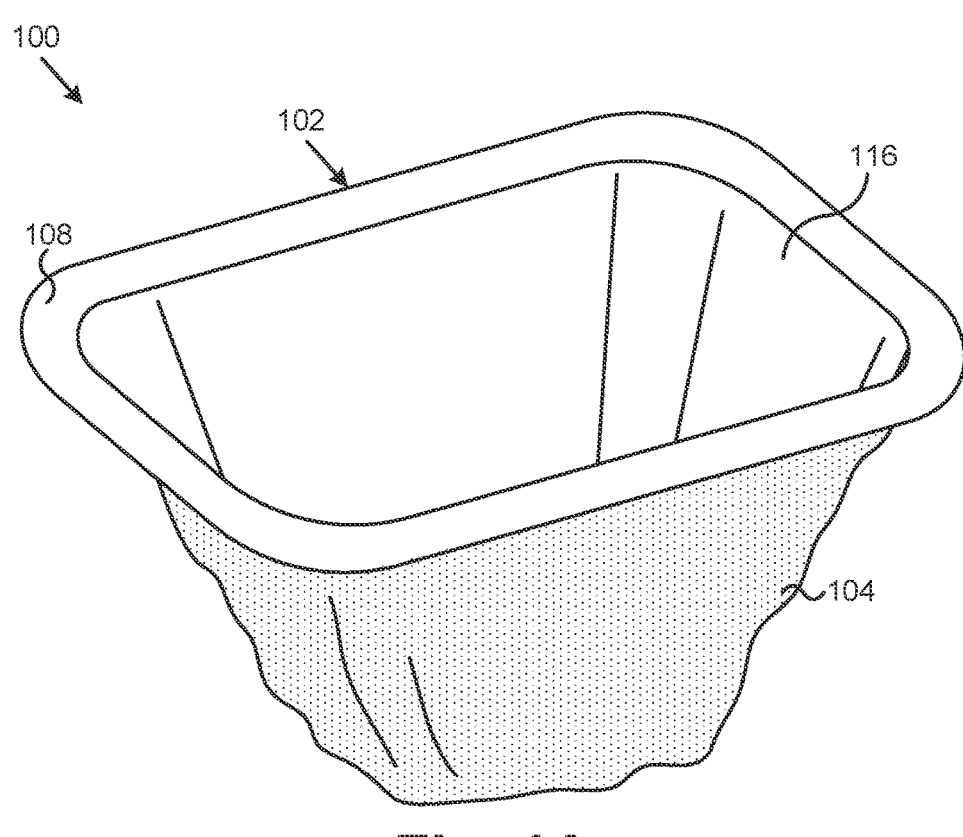
FIG. 1A shows a perspective view of an exemplary temperature-protective package, according to one implementation of the present application.
FIG. 1B shows a cross-sectional view corresponding to FIG. 1A.

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

FIG. 1A shows a perspective view of an exemplary temperature-protective package, according to one implementation of the present application. FIG. 1B shows a cross-sectional view corresponding to FIG. 1A. As shown in FIGS. 1A and 1B, temperature-protective package 100 includes rigid container 102, flexible liner 104, and pocket 106.

Rigid container 102 includes rim 108, interior 110, exterior 112, contours 114, and cavity 116. Rigid container 102 protects temperature-sensitive product 118 from external forces. Rigid container 102 can be formed from any rigid material, such as, for example, polyethylene terephthalate (PET), PET copolymers like PET glycol-modified (PET-G), or polypropylene (PP).

Rim 108 is configured for sealing cavity 116, and defines interior 110 and exterior 112 of rigid container 102. For example, in the present implementation, a lid (not shown) can be attached to the top of rim 108 using an adhesive. In various implementations, the lid is formed from a gas-permeable material, such as TYVEK®, or a gas-impermeable material. In one implementation, the lid is formed from the same material as rigid container 102. In various implementations, rim 108 may have a different shape, or may seal cavity 116 in a different manner. For example, rim 108 may seal with a lid in a clamshell configuration. Rim 108 may be configured to seal mechanically using mating means and/or a gasket, rather than using an adhesive.

Rigid container 102 utilizes cavity 116 to receive temperature-sensitive product 118. Temperature-sensitive product 118 may be any product that can be damaged by exposure to temperatures that arm too low or too high. For example, temperature-sensitive product 118 may be a bioprosthetic heart valve that needs to be kept between approximately one degree Celsius and approximately forty-five degrees Celsius (1° C.-45° C.). In the present implementation, cavity 116 is shown to have an inverted trapezoidal pyramid shape and rounded contours 114. Although temperature-sensitive product 118 is illustrated a generic component in FIG. 1B, in other implementations, rigid container 102 may be shaped and contoured such that interior 110 conforms to temperature-sensitive product 118.

Flexible liner 104 is attached to rigid container 102. In particular, flexible liner 104 is attached to the bottom of rim 108 on exterior 112 of rigid container 102. Flexible liner 104 forms pocket 106 between itself and rigid container 102. Flexible liner 104 can be formed from any flexible material, such as, for example, medium-density or low-density polyethylene (PE). Flexible liner 104 may be attached by any technique known in the art, such as plastic welding or pressure-sensitive adhesives.

Phase change material (PCM) is situated in pocket 106. As used herein, "PCM" refers to any latent heat storage material. At a characteristic phase change temperature, the PCM in pocket 106 is able absorb a certain capacity of heat energy without increasing in temperature, due to its latent heat storage property. As a result, the PCM in pocket 106 can keep temperature-sensitive product 118 in temperature-protective package 100 cool when exposed to heat energy. In various implementations. PCM situated in pocket 106 comprises a paraffin hydrocarbon or a salt hydrate. In one implementation, the phase change temperature of the PCM closely matches the temperature-sensitivity of temperature-sensitive product 118. Continuing the above example, the PCM in pocket 106 may have a melting point of approximately forty-five degrees Celsius (45° C.). The material for the PCM may also be chosen based on latent heat storage capacity, thermal conductivity, volume expansion, and other factors. In the present implementation, the PCM in pocket 106 is made of solid granules or powder. In one implementation, pocket 106 is filled with PCM without any encapsulating or intervening materials, such that PCM directly contacts exterior 112 (except negligible volumes of air or vacuum between granules).

The PCM in pocket 106 conforms to a contoured surface of rigid container 102. In particular, the PCM in pocket 106 conforms to contoured exterior 112. As used herein, a "contour" or a "contoured surface" refers to any surface having a curvature, angle, or bend such that it is not substantially straight. Flexible liner 104 is flexible enough to be bent around contours 114 of rigid container 102. Flexible liner 104 is also resilient enough that the weight of the PCM alone does not cause it to sag into a focal point. Rather, the PCM conforms to the contoured surface of exterior 112 between the points where flexible liner 104 is attached to rigid container 102. In the present implementation, the PCM in pocket 106 conforms to substantially the entire exterior 112 of rigid container 102. As a result, the PCM maximizes temperature protection to temperature-sensitive product 118 from external heat sources. As used herein, "substantially an entire exterior" may refer to the exterior minus any portions utilized as sealing means, such as rim 108. In various implementations, a flexible liner and conforming PCM may be provided to more or fewer portions of rigid container 102. For example, where rigid container 102 is configured to be sealed using a clamshell lid, as described above, the clamshell lid may have a flexible liner attached thereto, creating a pocket of PCM that conforms thereto. In various implementations, the flexible liner may be attached to interior 110 of rigid container 102. In one implementation, rigid container 102 can include supporting legs, posts, or platforms, (not shown) or any other structures that prevent flexible liner 104 from directly contacting the ground. For example, a stand having an "L-shaped" cross-section that is taller than rigid container 102 can be attached to the bottom of rim 108, to create a gap below flexible liner 104.

Temperature-protective package 100 is able to provide several advantages. The latent heat storage property of the PCM in pocket 106 provides temperature protection for temperature-sensitive product 118. The PCM in pocket 106 is also generally less dense than traditional gel refrigerants, generally reducing the weight of temperature-protective package 100. Further, because the PCM in pocket 106 conforms to contoured surfaces of rigid container 102, temperature-protective package 100 minimizes volume and bulk.

Figure 2A:
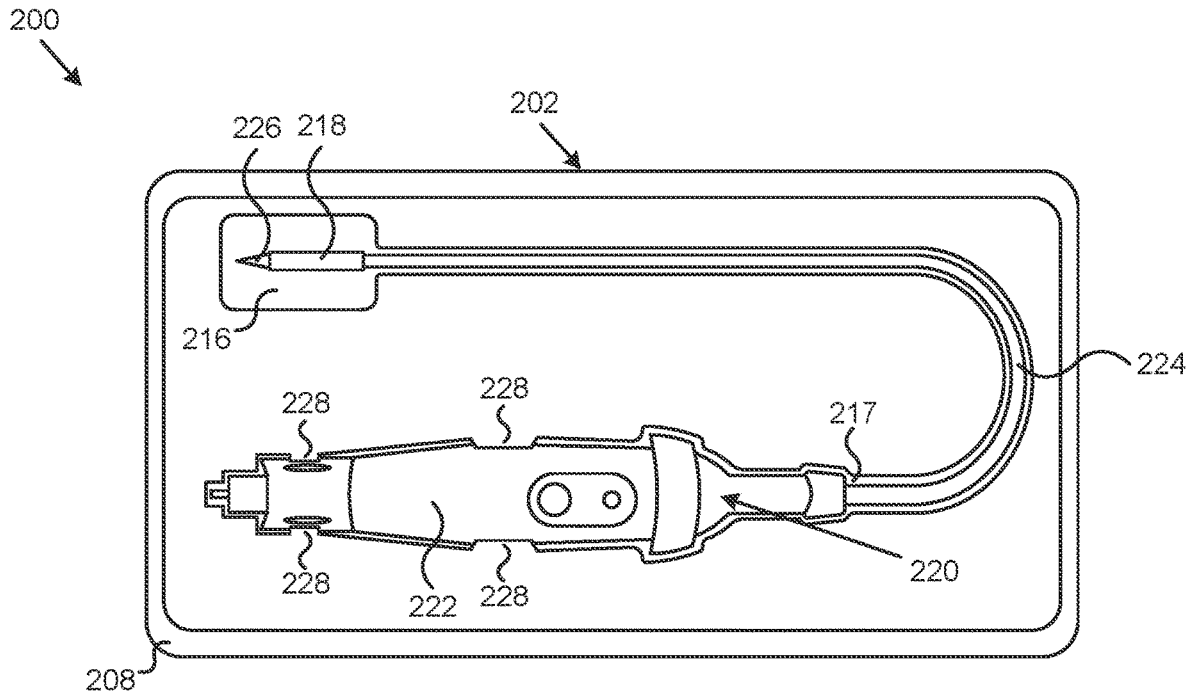
FIG. 2A shows a top view of an exemplary temperature-protective package, according to one implementation of the present application.
Figure 2B:
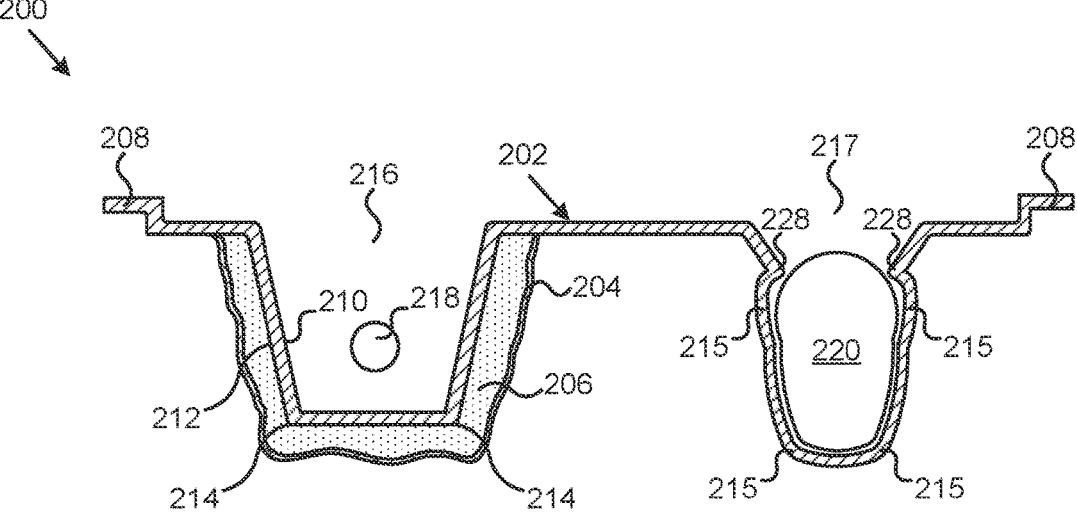
FIG. 2B shows a cross-sectional view corresponding to FIG. 2A.

FIG. 2A shows a top view of an exemplary temperature-protective package, according to one implementation of the present application. FIG. 2B shows a cross-sectional view corresponding to FIG. 2A. As shown in FIGS. 2A and 2B, temperature-protective package 200 includes rigid container 202, flexible liner 204, and pocket 206. Rigid container 202 includes rim 208, interior 210, exterior 212, contours 214 and 215, cavities 216 and 217, and securing tabs 228. Except for differences noted below, rigid container 202, flexible liner 204, pocket 206, rim 208, interior 210, exterior 212, contours 214, and cavity 216 in FIGS. 2A and 2B generally correspond to rigid container 102, flexible liner 104, pocket 106, rim 108, interior 110, exterior 112, contours 114, and cavity 116 in FIGS. 1A and 1B, and may have any implementations and advantages described above.

In FIGS. 2A and 2B, cavity 216 of rigid container 202 is configured to receive temperature-sensitive product 218 and cavity 217 of rigid container 202 is configured to receive non-temperature-sensitive product 220. Temperature-sensitive product 218 is attached to non-temperature-sensitive product 220, and as such, they are provided as an integrated product. In the present implementation, temperature-sensitive product 218 is a heart valve, and non-temperature-sensitive product 220 to which it is attached is a steerable transcatheter delivery system. Non-temperature-sensitive product 220 includes handheld motor/steering portion 222, steerable catheter 224, and guide tip 226. Temperature-sensitive product 218 and non-temperature-sensitive product 220 may have additional components and details not shown in FIGS. 2A and 2B. In other implementations, temperature-sensitive product 218 and non-temperature-sensitive product 220 to which it is attached may be products other than a heart valve and a steerable transcatheter delivery system. Advantageously, by providing temperature-sensitive product 218 and non-temperature-sensitive product 220 pre-attached, temperature-protective package 200 reduces assembly time, and reduces the possibility of contaminating or damaging temperature-sensitive product 218 during assembly.

In the present implementation, cavity 216 is shown to have an inverted trapezoidal pyramid shape and rounded contours 214. Cavity 217 is shown to be a channel with contours 215 matching the sides and bottom of non-temperature-sensitive product 220. Securing tabs 228 secure handheld motor/steering portion 222 on the top of non-temperature-sensitive product 220. Temperature-protective package 200 may utilize more or fewer securing tabs 228, or means of securing non-temperature-sensitive product 220 as known in the art. As seen in the top view of FIG. 2A, rigid container 202 also includes contours such that cavity 217 redirects steerable catheter 224 one-hundred-eighty degrees (180°). Because steerable catheter 224 is narrow and, in practice, may be much longer than shown in FIG. 2A, redirecting it in this manner can reduce dimensions of temperature-protective package 200.

Flexible liner 204 is attached to exterior 212 of rigid container 202 around cavity 216, and forms pocket 206 between itself and rigid container 202. As described above. PCM is situated in pocket 206. The PCM in pocket 206 conforms around contours 214 corresponding to cavity 216 which receives temperature-sensitive product 218. In contrast, no flexible liner is attached to rigid container 202 around cavity 217. No PCM conforms around contours 215 corresponding to cavity 217 which receives non-temperature-sensitive product 220. Thus, temperature-protective package 200 can provide temperature protection for temperature-sensitive product 218 and accommodate integrated non-temperature-sensitive product 220, while maintaining light weight and small form factor.

Figure 3A:
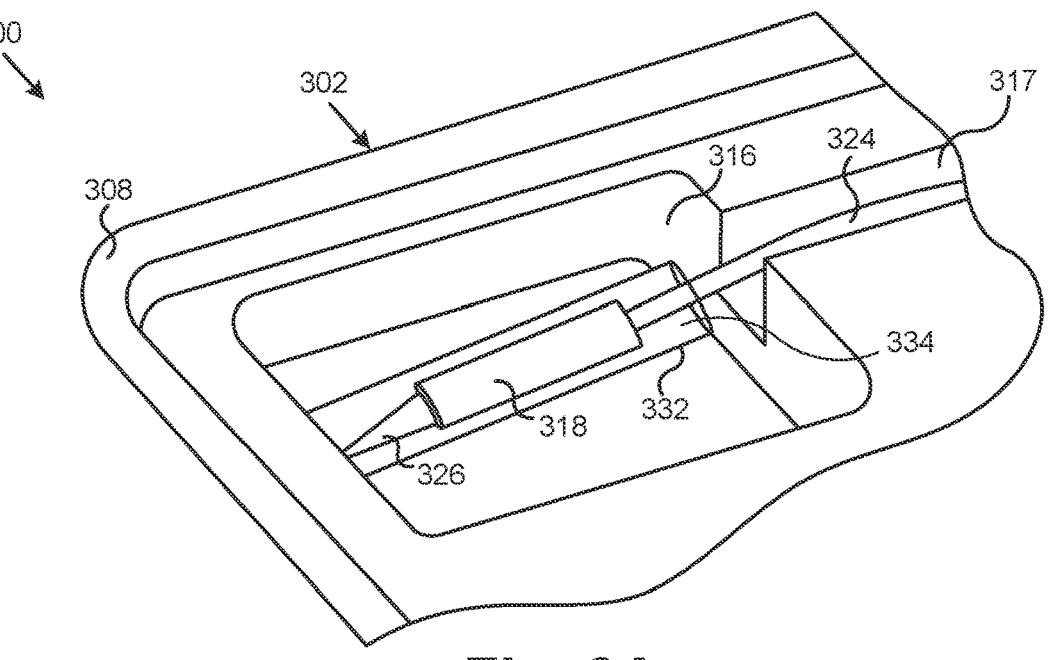
FIG. 3A shows a perspective view of a portion of an exemplary temperature-protective package, according to one implementation of the present application.
Figure 3B:
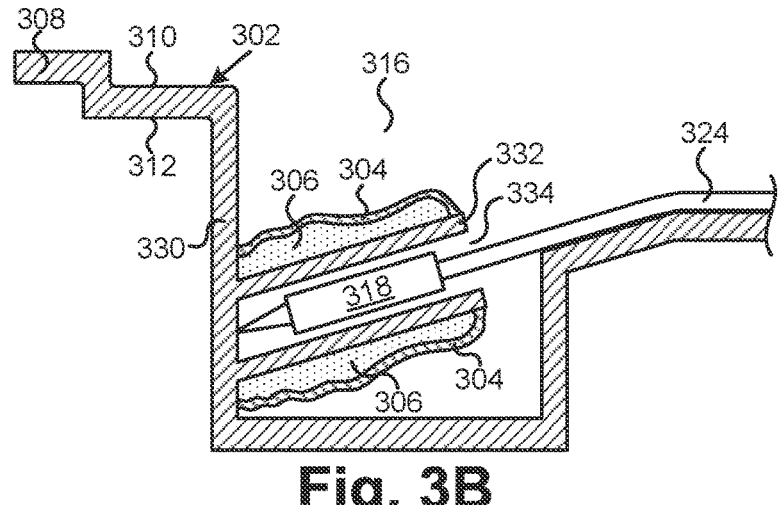
FIG. 3B shows a cross-sectional view corresponding to FIG. 3A.

FIG. 3A shows a perspective view of a portion of an exemplary temperature-protective package, according to one implementation of the present application. FIG. 3B shows a cross-sectional view corresponding to FIG. 3A. As shown in FIGS. 3A and 3B, temperature-protective package 300 includes rigid container 302 having rim 308, interior 310, exterior 312, cavities 316 and 317, sidewall 330, and cylindrical contour 332 having cylindrical cavity 334. Also shown in FIGS. 3A and 3B are temperature-sensitive product 318, and steerable catheter 324 and guide tip 326 of a non-temperature-sensitive product. Except for differences noted below, rigid container 302, rim 308, interior 310, exterior 312, cavities 316 and 317, temperature-sensitive product 318, steerable catheter 324, and guide tip 326 in FIGS. 3A and 3B generally correspond to rigid container 202, rim 208, interior 210, exterior 212, cavities 216 and 217, temperature-sensitive product 218, steerable catheter 224, and guide tip 226 in FIGS. 2A and 2B, and may have any implementations and advantages described above.

In FIGS. 3A and 3B, cylindrical contour 332 is situated on interior 310 of rigid container 302, inside cavity 316. Cylindrical contour 332 protrudes from sidewall 330 towards interior 310, forming cylindrical cavity 334. Cylindrical cavity 334 receives temperature-sensitive product 318. Because temperature-sensitive product 318 is substantially cylindrical, cylindrical cavity 334 more closely matches the shape of temperature-sensitive product 318, limiting jostling and possible damage of temperature-sensitive product 318 during transportation of temperature-protective package 300. In the present implementation, cylindrical cavity 334 also receives and guides tip 326 and also a portion of steerable catheter 324, which are attached to temperature-sensitive product 318. Cylindrical contour 332 may form any angle with sidewall 330. In one implementation, the angle between sidewall 330 and cylindrical contour 332 may be forty-five degrees (45°) or less, such that more weight is distributed on guide tip 326 than temperature-sensitive product 318.

As shown in FIG. 3B, flexible liner 304 is attached to interior 310 of rigid container 302 around cylindrical cavity 334. In particular, flexible liner 304 is attached to sidewall 330 and a tip of cylindrical contour 332 opposite sidewall 330. Flexible liner 304 forms pocket 306 between itself and cylindrical contour 332. As described above. PCM is situated in pocket 306. The PCM in pocket 306 conforms around cylindrical contour 332 corresponding to cylindrical cavity 334 which receives temperature-sensitive product 318. Thus, temperature-protective package 300 can provide more efficient temperature protection for temperature-sensitive product 318. It is noted that, for purposes of illustration, flexible liner 304 is not shown in the perspective view of FIG. 3A, and various components are illustrated as seen-through cylindrical contour 332. However, it is noted that temperature-protective package 300 in FIG. 3A may also include flexible liner 304, and flexible liner 304 and/or cylindrical contour 332 may be transparent or opaque. In one implementation, in another flexible liner (in addition to flexible liner 304), such as flexible liner 204 in FIG. 2B, may be attached to exterior 312 of rigid container 302 around cavity 316, in order to provide increased temperature protection.

Figure 3C:
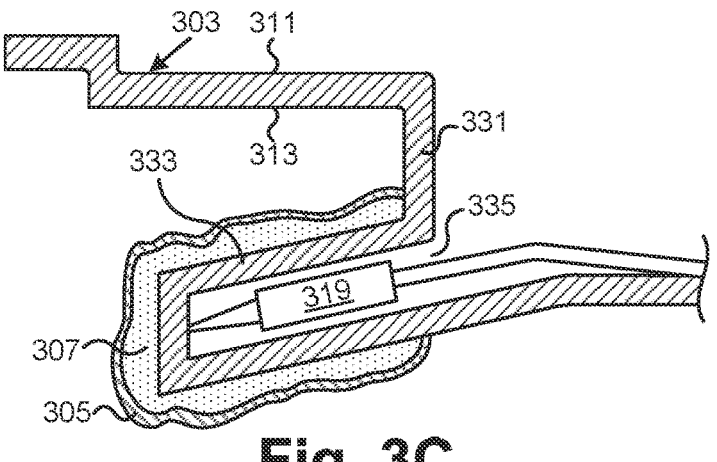
FIG. 3C shows a cross-sectional view of a portion of an exemplary temperature-protective package, according to one implementation of the present application.

FIG. 3C shows a cross-sectional view of a portion of an exemplary temperature-protective package, according to one implementation of the present application. FIG. 3C represents an alternative implementation to FIGS. 3A and 3B where cylindrical contour 333 protrudes from sidewall 331 towards exterior 313, while still forming cylindrical cavity 335 on interior 311. As shown in FIG. 3C, flexible liner 305 is attached to exterior 313 of rigid container 303 around cylindrical cavity 335. The PCM in pocket 307 conforms around cylindrical contour 333 corresponding to cylindrical cavity 335 which receives temperature-sensitive product 319.

Figures 4A, 4B, 4C:
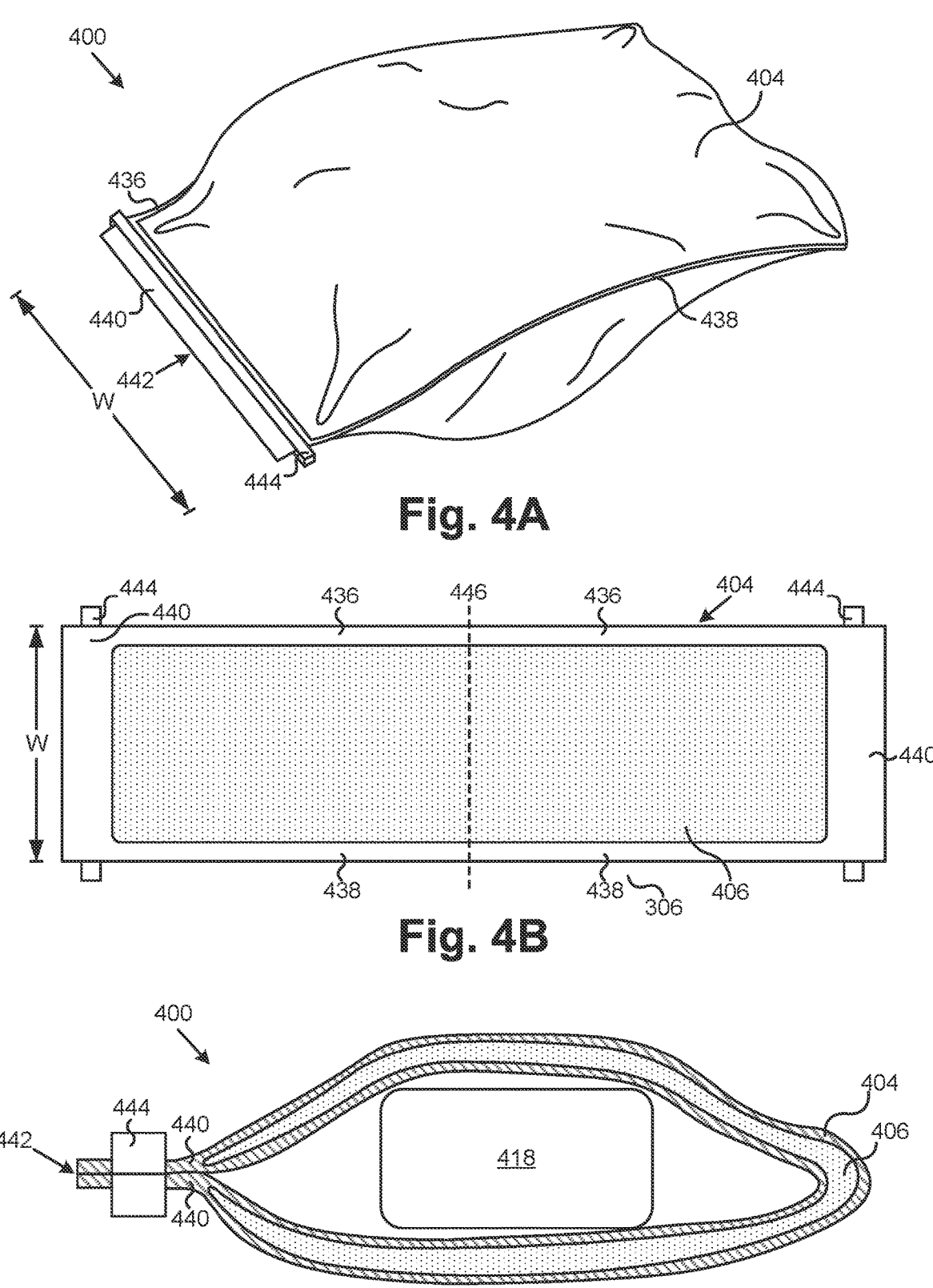
FIG. 4A shows a perspective view of an exemplary temperature-protective package, according to one implementation of the present application.
FIG. 4B shows a plan view corresponding to FIG. 4A.
FIG. 4C shows a cross-sectional view corresponding to FIG. 4A.

FIG. 4A shows a perspective view of an exemplary temperature-protective package, according to one implementation of the present application. FIG. 4B shows a plan view corresponding to FIG. 4A. FIG. 4C shows a cross-sectional view corresponding to FIG. 4A. Temperature-protective package 400 includes flexible liner 404 having edges 436, 438.440, pocket 406 of PCM, opening 442, and seal 444. Also shown in FIG. 4C is product 418.

The temperature-protective packages shown in FIGS. 1A through 3C utilize a flexible liner attached to a rigid container. In contrast, temperature-protective package 400 in FIGS. 4A through 4C may utilize flexible liner 404 without a rigid container. As shown in FIG. 4C, pocket 406 of PCM is within flexible liner 404, rather than between a flexible liner and a rigid container. Pocket 406 may be formed within flexible liner 404, for example, by plastic welding two sheets of polyethylene (PE) around PCM material. As described above, any suitable flexible material and suitable PCM material may be used. After welding, the result may look similar to FIG. 4B. Edges 436, 438, and 440 may indicate where portions of the PE sheets were welded. In the present implementation, as shown in FIG. 4B, flexible liner 404 is substantially rectangular prior to being formed into temperature-protective package 400. In various implementations, flexible liner 404 may have any other initial shape.

Next, flexible liner 404 may be folded along fold line 446. Edges 436 may be fused to each other, and edges 438 may be fused to each other. Edges 436 and 438 may be fused by any technique known in the art, such as plastic welding or pressure-sensitive adhesives. After folding and fusing, flexible liner 404 defines a preferred shape of temperature-protective package 400, corresponding to fold line 446 and fused edges 436 and 438. In particular, because fused edges 436 and 438 are substantially linear and parallel, the preferred shape of temperature-protective package 400 is substantially rectangular with width W. As described further below, the preferred shape can also be understood as a shape for which temperature-protective package 400 minimizes flexing and maximizes conforming upon receiving a product.

Flexible liner 404 also defines opening 442 for receiving product 418. Opening 442 corresponds to the preferred shape of temperature-protective package 400. Unfused edges 440 opposite fold line 446 define opening 442. In particular, because unfused edges 440 meet fused edges 436 and 438 at two portions, opening 442 is substantially slit-like. Opening 442 corresponds to the preferred shape of temperature-protective package 400 in that a product having the preferred shape can be received with minimal flexing of opening 442. For example, in the present implementation, since the preferred shape of temperature-protective package 400 is substantially rectangular with width W, opening 442 may receive a substantially flat rectangular product or an envelope-like product having width W or less with little to no flexing of slit-like opening 442. However, when receiving a spherical product or rectangular prism product, opening 442 may flex more, such that opening 442 is eyelid-like or ellipse-like.

When receiving product 418, flexible liner 404 may also flex about the preferred shape. For example, when a product having the preferred shape is inserted, flexible liner 404 may closely conform to the product with little to no flexing. Continuing the above example of receiving an envelope-like product, flexible liner 404 may conform to substantially the entirety of the product. Meanwhile, when a product not having the preferred shape is inserted, flexible liner 404 may flex more, and less closely conform to the product. The result may look similar to FIGS. 4A and 4C. FIGS. 4A and 4C may illustrate receiving a rectangular prism product 418. Flexible liner 404 flexes out from its substantially flat rectangular preferred shape to fit product 418, but flexible liner 404 conforms more to the top and bottom of product 418 than to its sides. Thus, the preferred shape of temperature-protective package 400 may refer to a shape that minimizes flexing of flexible liner 404 and maximizes conforming of flexible liner 404 to a received product. Advantageously, pocket 406 of PCM will flex and conform as flexible liner 404 does. Thus, temperature-protective package 400 maximizes temperature protection and minimizes bulk for products of a preferred shape, while still being able to provide temperature protection and reduced bulk for other products due to flexible liner 404.

After receiving product 418, opening 442 may be sealed by seal 444. Seal 444 may utilize any sealing technique known in the art, such as a clamp or pressure seal. In the present implementation, seal 444 is reversible, such that temperature-protective package 400 can be re-opened without permanent damage. In the present implementation, seal 444 forms around the outsides of edges 440, with one sealing member on each of edges 440. In various implementations, seal 444 may be formed on the insides of edges 440 and/or may use more of fewer sealing members.

Figure 5:
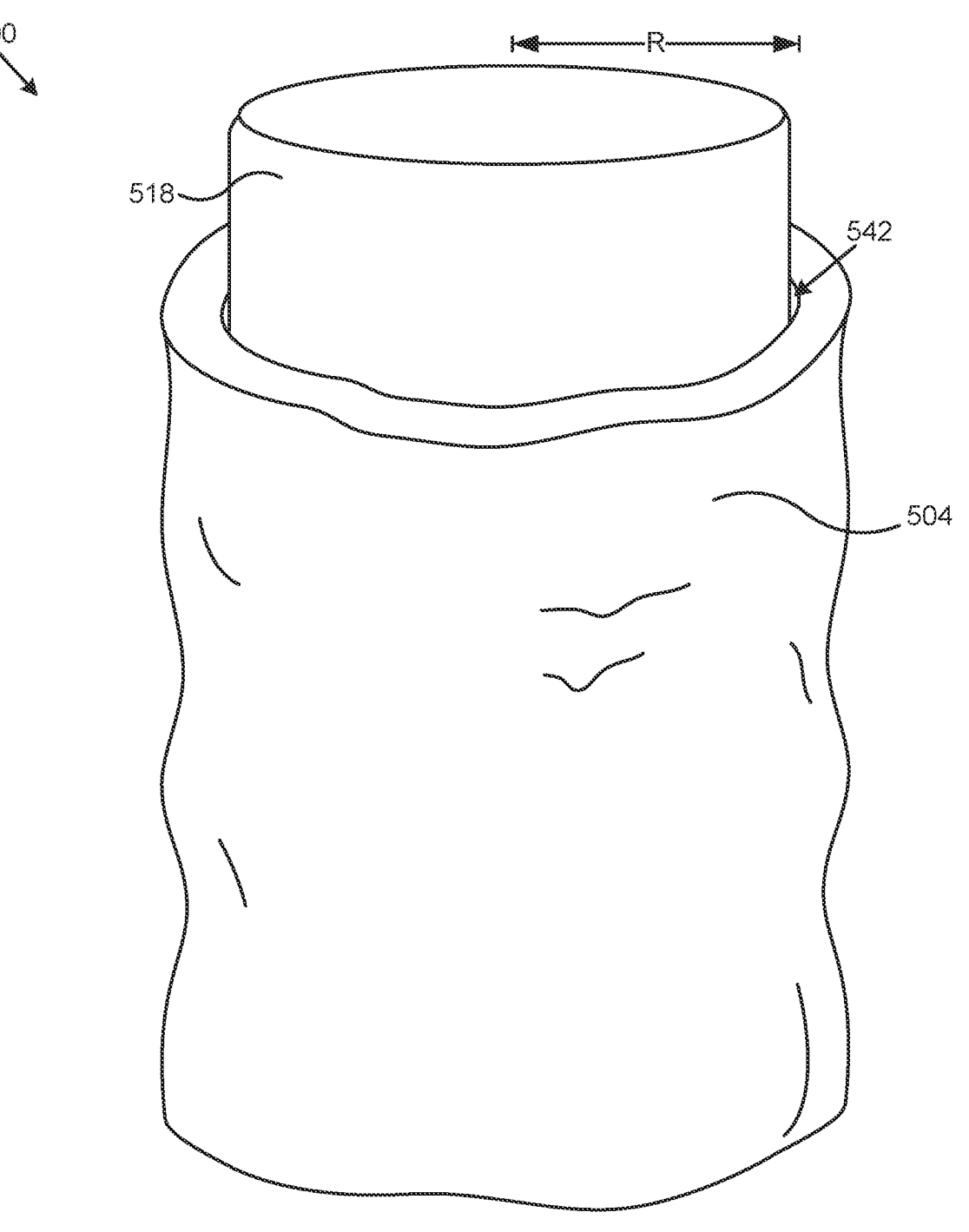
FIG. 5 shows a perspective view of an exemplary temperature-protective package, according to one implementation of the present application.

FIG. 5 shows a perspective view of an exemplary temperature-protective package, according to one implementation of the present application. Temperature-protective package 500 includes flexible liner 504 and opening 542. A pocket of PCM is within flexible liner, as described above. Also shown in FIG. 5 is product 518.

In the present implementation, flexible liner 504 defines a substantially cylindrical preferred shape of temperature-protective package 500. Flexible liner 504 also defines opening 542 for receiving product 518. In particular, opening 542 is substantially circular. Opening 542 corresponds to the preferred shape of temperature-protective package 500 in that a product having the preferred shape can be received with minimal flexing of opening 542. For example, in the present implementation, since the preferred shape of temperature-protective package 500 is substantially cylindrical with radius R, opening 542 may receive cylindrical product 518 having radius R or less with little to no flexing of circular opening 542. However, when receiving a rectangular prism product, opening 542 may flex more.

Temperature-protective package 500 in FIG. 5 is also shown without a seal. Cylindrical product 518 is longer than temperature-protective package 500 and protrudes from opening 542. Nonetheless, temperature-protective package 500 still provides temperature protection and reduced bulk. In various implementations, temperature-protective package 500 may seal product 518. For example, temperature-protective package 500 may be longer than product 518 and opening 542 may be sealed similar to FIG. 4A. As yet another example, another temperature-protective package having a substantially cylindrical preferred shape may fit over top of product 518 and seal against the outside, top, or inside of temperature-protective package 500.

Figure 6A:
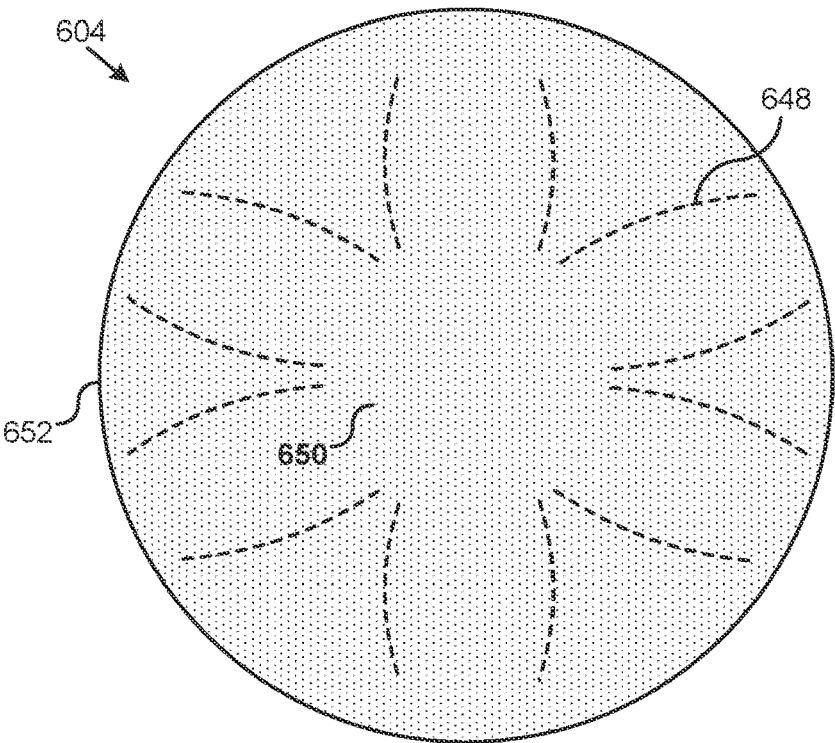
FIG. 6A shows a plan view corresponding to FIG. 5.
Figure 6B:
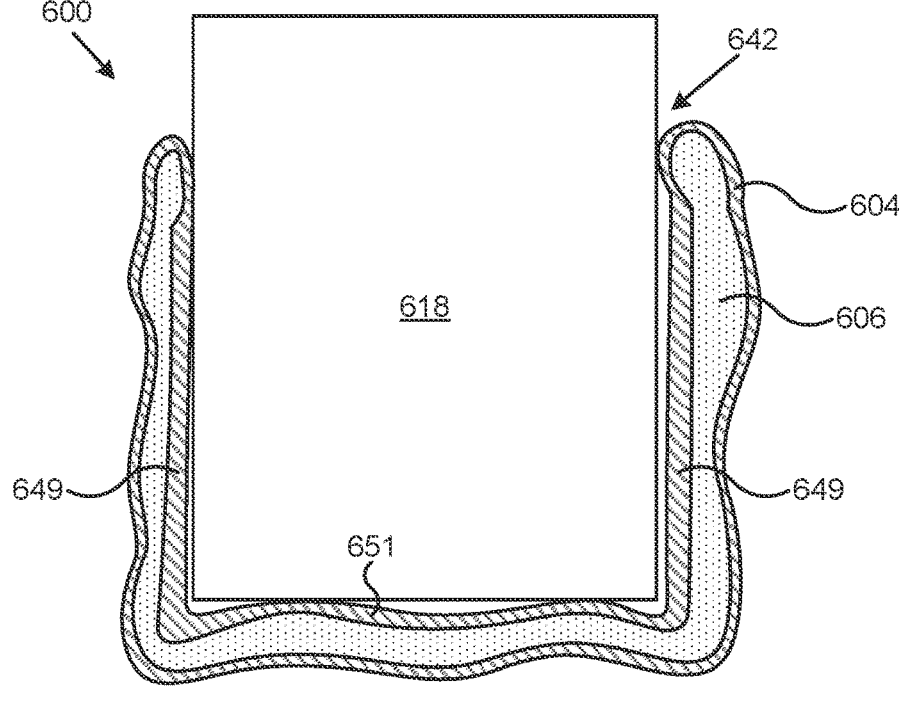
FIG. 6B shows a cross-sectional view corresponding to FIG. 5.

FIG. 6A shows a plan view corresponding to FIG. 5. FIG. 6B shows a cross-sectional view corresponding to FIG. 5. Temperature-protective package 600 in FIG. 6B generally corresponds to temperature-protective package 500 in FIG. 5. In the present implementation, as shown in FIG. 6A, flexible liner 604 is substantially circular prior to being formed into temperature-protective package 600. Flexible liner 604 may be formed, for example, from circular sheets of PE around PCM material. Next, flexible liner 604 may be crimped between inner circular region 650 and its perimeter 652 at regular radial intervals, as indicated by crimp lines 648, thereby defining the preferred substantially cylindrical shape of temperature-protective package 600.

As shown in FIG. 6B, crimped portions 649 (corresponding to crimp lines 648 in FIG. 6A) of flexible liner 604 define the sidewalls of the preferred substantially cylindrical shape of temperature-protective package 600 as well as opening 642. Bottom portion 651 of flexible liner 604 (corresponding to inner circular region 650 in FIG. 6A) defines the bottom of the preferred substantially cylindrical shape of temperature-protective package 600. Thus, when receiving cylindrical product 618 having the preferred shape, flexible liner 604, and thus pocket 606 of PCM, may closely conform to cylindrical product 618 with little to no flexing.

Figure 7A:
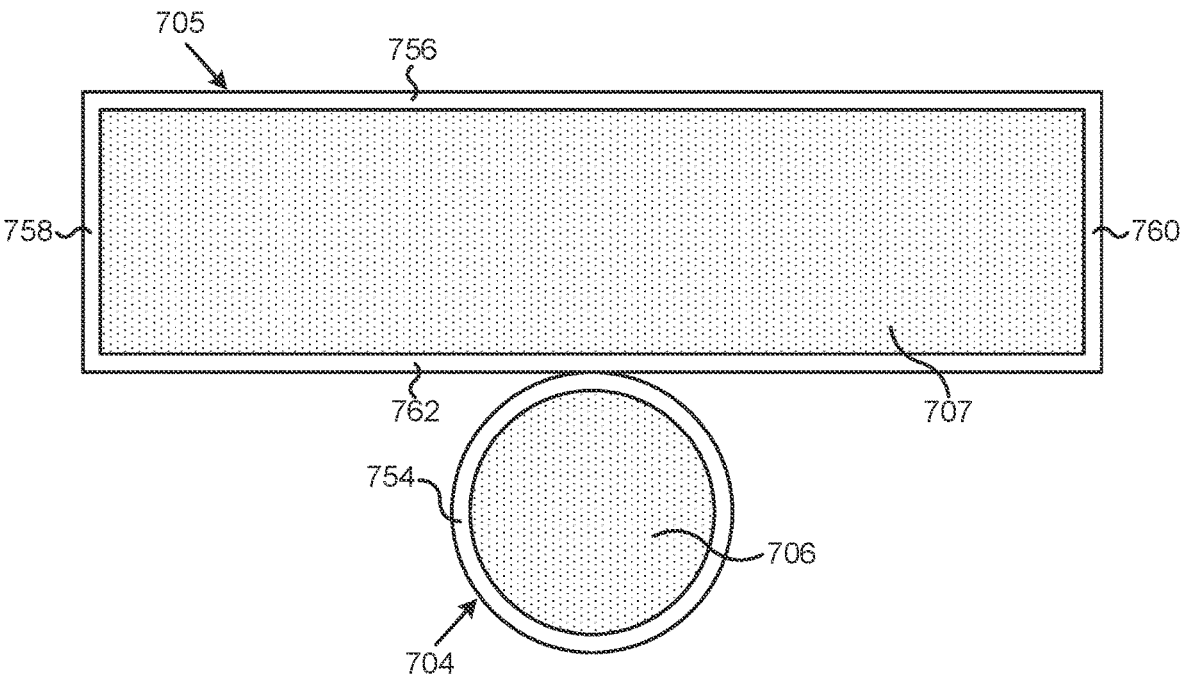
FIG. 7A shows a plan view corresponding to FIG. 5.
Figure 7B:
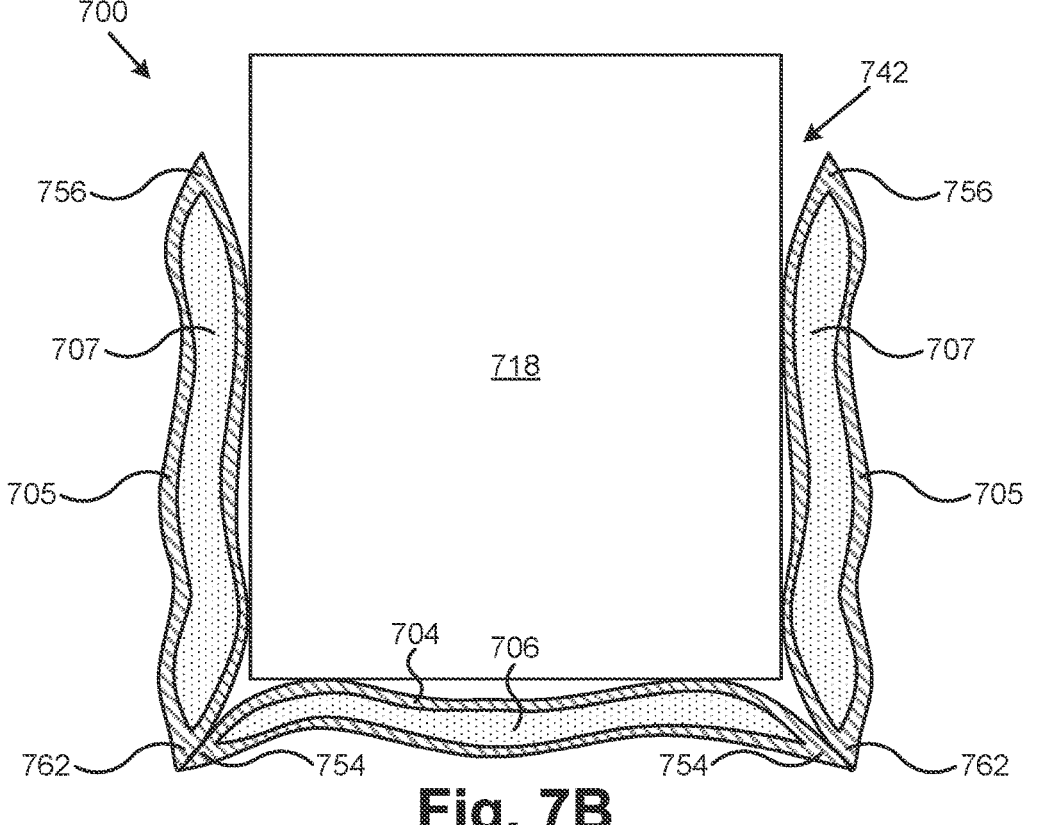
FIG. 7B shows a cross-sectional view corresponding to FIG. 5.

FIG. 7A shows a plan view corresponding to FIG. 5. FIG. 7B shows a cross-sectional view corresponding to FIG. 5. Temperature-protective package 700 in FIG. 7B generally corresponds to temperature-protective package 500 in FIG. 5. Referring back to FIGS. 4A through 4C above, a single flexible liner 404 was utilized to define the preferred shape and opening 442. In contrast, in FIGS. 7A and 7B, multiple flexible liners are utilized to define the preferred shape of temperature-protective package 700 and opening 742.

In the present implementation, as shown in FIG. 7A, flexible liner 704 has edge 754 and is substantially circular prior to being formed into temperature-protective package 700. Flexible liner 704 may be formed, for example, from circular sheets of PE around PCM material. Flexible liner 705 has edges 756, 758, 760, and 762 and is substantially rectangular prior to being formed into temperature-protective package 700. Flexible liner 705 may be formed, for example, from rectangular sheets of PE around PCM material.

Next, flexible liner 705 may be curled. Edges 758 and 760 of flexible liner 705 may be fused to each other. And edge 762 of flexible liner 705 may be fused to edge 754 of flexible liner 704. Edges may be fused by any technique known in the art, as described above. Thus, flexible liners 704 and 705 together define the preferred substantially cylindrical shape of temperature-protective package 700 using fused edges from both flexible liners 704 and 705.

Referring to FIG. 7B, fused edge 762 of flexible liner 705 and fused edge 754 of flexible liner 704 defines the bottom of the preferred substantially cylindrical shape of temperature-protective package 70). Fused edges 758 and 760 of flexible liner 705 (not visible in the cross-section of FIG.

7B) define the sidewalls of the preferred substantially cylindrical shape of temperature-protective package 700. Fused edges 758 and 760 of flexible liner 705 (not visible in the cross-section of FIG. 7B), together with unfused edge 756 of flexible liner 705, define opening 742. Thus, when receiving cylindrical product 718 having the preferred shape, flexible liners 704 and 705, and thus pockets 706 and 707 of PCM, may closely conform to cylindrical product 718 with little to no flexing.

In various implementations, multiple flexible liners can be utilized to define various preferred shapes of a temperature-protective package. For example, five flexible liners that are substantially rectangular prior to being formed into a temperature-protective package can be fused at edges to produce a temperature-protective package having a substantially rectangular prism preferred shape and a rectangular opening. In this implementation, the temperature-protective package may receive, closely conform to, and optionally seal, a rectangular prism product, such as product 418 in FIG. 4C. In various implementations, temperature-protective packages similar to those in FIGS. 4A through 7B may have preferred shapes corresponding to rigid containers similar to those in FIGS. 1A through 3C. For example, a temperature-protective package system may include a temperature-protective package similar to those in FIGS. 4A through 7B receiving temperature-protective package 200 in FIGS. 2A and 2B.

Thus, the present application discloses various implementations of temperature-protective packages with shape-conforming PCM. From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described herein, but many rearrangements, modifications, and substitutions are possible without departing from the scope of the present disclosure.

What is claimed is:

1. A temperature-protective package comprising:
a container comprising:
    a first cavity comprising contours forming a bottom of the first cavity, the first cavity sized to receive a temperature-sensitive product;
    a second cavity sized to receive a non-temperature-sensitive product attached to the temperature-sensitive product; and
    a rim extending in parallel with the bottom of the first cavity;
a liner attached to the rim such that a pocket is formed between the container and the liner, wherein the liner is composed of different material than the first cavity and flexibly bends around the contours of the first cavity, wherein the liner is attached to the rim around the first cavity, and wherein no liner is attached to the container around the second cavity; and
phase change material (PCM) situated in the pocket;
wherein the PCM conforms to a contoured surface of the container.

2. The temperature-protective package of claim 1, wherein the PCM comprises a paraffin hydrocarbon or a salt hydrate.

3. The temperature-protective package of claim 1, wherein the PCM has a phase change temperature of approximately forty-five degrees Celsius (45° C.).

4. The temperature-protective package of claim 1, wherein the liner is attached to an exterior of the container.

5. The temperature-protective package of claim 1, wherein the contoured surface to which the PCM conforms corresponds to the first cavity.

6. The temperature-protective package of claim 1, further comprising a channel extending between the first cavity and the second cavity.

7. The temperature-protective package of claim 6, wherein the channel is sized to receive a tube extending between the non-temperature-sensitive product and the temperature-sensitive product.

8. The temperature-protective package of claim 1, wherein the rim extends between the first cavity and the second cavity.

9. The temperature-protective package of claim 1, wherein the first cavity has a different shape than the second cavity.

10. The temperature-protective package of claim 1, wherein the liner flexibly conforms to the contoured surface of the container.

11. A temperature-protective package comprising:
a container comprising a first cavity sized to receive a temperature-sensitive product and a second cavity sized to receive a non-temperature-sensitive product, the first cavity decreasing in width from an opening of the first cavity to a bottom of the first cavity;
a channel extending between the first cavity and the second cavity;
a liner attached to the container such that a pocket is formed between the first cavity and the liner, wherein the liner is composed of different material than the first cavity; and
phase change material (PCM) situated in the pocket;
wherein the liner and the PCM conform to a contoured surface of the container, wherein the liner is attached to the container around the first cavity, and wherein no liner is attached to the container around the second cavity.

12. The temperature-protective package of claim 11, wherein the liner is attached to an exterior of the container.

13. The temperature-protective package of claim 11, wherein the contoured surface to which the PCM conforms corresponds to the first cavity.

14. The temperature-protective package of claim 11, wherein the liner flexibly conforms to the contoured surface of the container.

15. The temperature-protective package of claim 11, wherein the container comprises a rim extending in parallel with the bottom of the first cavity, and wherein the liner is attached to the rim.

16. The temperature-protective package of claim 11, wherein the first cavity has a different number of sides than the second cavity at the opening of the first cavity.

17. A temperature-protective package comprising:
a container comprising a first cavity sized to receive a temperature-sensitive product and a second cavity sized to receive a non-temperature-sensitive product, the second cavity having a varying shape between an opening of the second cavity and a bottom of the second cavity;
a channel extending between the first cavity and the second cavity;

a liner attached to the container such that a pocket is formed between the first cavity and the liner, wherein the liner is composed of different material than the first cavity; and phase change material (PCM) situated in the pocket;

wherein the liner and the PCM conform to a contoured surface of the container, wherein the liner is attached to the container around the first cavity, and wherein no liner is attached to the container around the second cavity.

18. The temperature-protective package of claim 17, wherein the second cavity has a different number of sides than the first cavity at the opening of the second cavity.

\* \* \* \* \*